United States Patent [19]

Takagahara et al.

[11] 4,258,131
[45] Mar. 24, 1981

[54] METHOD OF FRACTIONAL QUANTITATIVE DETERMINATION OF ISOENZYME OF LACTIC DEHYDROGENASE

[75] Inventors: Isamu Takagahara, Kawanishi; Juniti Yamauti, Suita; Setsuko Yoshimura, Nara; Katsumi Fujii, Suita; Takekazu Horio, Takatsuki, all of Japan

[73] Assignee: Oriental Yeast Co. Ltd., Tokyo, Japan

[21] Appl. No.: 54,416

[22] Filed: Jul. 3, 1979

[30] Foreign Application Priority Data

Jul. 10, 1978 [JP] Japan .............................. 53-082979

[51] Int. Cl.³ .............................................. C12Q 1/32
[52] U.S. Cl. ..................................... 435/26; 252/408; 536/26
[58] Field of Search .......................... 435/26, 805, 810; 252/408 R; 536/26

[56] References Cited

U.S. PATENT DOCUMENTS

| | | | |
|---|---|---|---|
| 4,003,975 | 1/1977 | Lamprecht | 435/26 |
| 4,006,061 | 2/1977 | Weeks et al. | 435/26 |
| 4,080,263 | 3/1978 | Bernt et al. | 435/26 |

OTHER PUBLICATIONS

Godfredsen, S. E. & Ottesen, N. "1,6-Dihydro-NAD as an Humidity-Induced Lactate Dehydrogenase Inhibitor in NADH Preparations", Carlsberg Res. Com. vol. 43 (3), pp. 171-175, (1978).

Howell B. F. et al.; "Detection of Inhibitors in Reduced Nicotinamide Adenine Dinucleotide by Kinetic Methods", Clin. Chem., vol. 22, No. 10; pp. 1648-1654, (1976).

Biellmann J. F. et al., "Structure of Lactate Dehydrogenase Inhibitor Generated from Coenzyme"; Biochemistry, vol. 18, No. 7, pp. 1212-1216, (1979).

Grau U. et al., "Combined Coenzyme-Substrate Analogues of Various Dehydrogenases"; Biochemistry, vol. 17, No. 22, pp. 4621-4626, (1978).

Primary Examiner—Benoit Castel
Attorney, Agent, or Firm—Browdy and Neimark

[57] ABSTRACT

1,6-Dihydro nicotinamide adenine dinucleotide inhibits both H-type lactic dehydrogenase and M-type lactic dehydrogenase which are isoenzymes of lactic dehydrogenase, but the degree of inhibition thereof against H-type considerably differs from that against M-type. A ratio of H-type lactic dehydrogenase to M-type lactic dehydrogenase in serum can be measured by utilizing the difference of inhibition degree. Therefore we can diagnose the organ with trouble.

1 Claim, 3 Drawing Figures

METHOD OF FRACTIONAL QUANTITATIVE DETERMINATION OF ISOENZYME OF LACTIC DEHYDROGENASE

The present invention relates to a utilization of the compound of 1,6-dihydro nicotinamide adenine dinucleotide.

In general, it is known that lactic dehydrogenase (referred to hereinafter as LDH) is an enzyme which catalyzes the reversible reaction of pyruvic acid and lactic acid in the presence of nicotine amide adenine dinucleotide (referred to hereinafter as NAD) as coenzyme.

LDH is present in the human body and it is contained in extremely small amount in serum of normal and healthy humans, however, a remarkable rise of LDH occurs from a malignant tumor, a myocardial infarction, hepatitis and so forth, and also a specific change of LDH occurs in accordance with aggravation and favorable turn of various diseases, so that a measurement of the LDH activity is very useful for the course observation of diseases and the decision in whether or not to undertake a particular therapeutic course.

Moreover, as to the human LDH, there are 2 kinds of enzymes (subunits): H-type (myocardial type: referred to hereinafter as H-type) and M-type (skeletal muscular type: referred to hereinafter as M-type), and ordinarily LDH exists as tetramer of these subunits. Since there are 2 kinds of subunits, 5 kinds of combination can be formed, and as a result, these 5 kinds ($H_4$, $H_3M$, $H_2M_2$, $HM_3$, $M_4$) are present as the isoenzymes of LDH. LDH elevations in serum occur due to the release of LDH from traumatized organs. For example in the case of hepatitis, most LDH released into serum is the M-type LDH derived from liver, and in case of myocardial infarction, most present is H-type LDH derived from heart. Therefore, the organ under stress can be detected by fractional quantitative determination such as electrophoresis of the isoenzyme of LDH released into serum.

As described above, the measurement of LDH activity has been very often utilized for clinical diagnosis, however, a prior determination method of LDH activity uses pyruvic acid and NADH, respectively as substrate and coenzyme, and then they are simply added in serum, and thereafter the decreasing amount of NADH is determined at 340 nm, thereby obtaining the total LDH activity.

In accordance with this prior method, it is possible to determine only whether the LDH activity is high or low, in other words, it is only possible to estimate the existence of disease somewhere in human body, therefore it is impossible to accurately identify diseased organs in the human body.

Although it is possible to carry out the fractional quantitative determination of isoenzyme of LDH by electrophoresis in order to identify the organ under stress, a weak point in this electrophoretic method is the fact that it requires very long time since it depends upon extremely complicated techniques, and therefore a more simple measuring method is desirable.

The inventors of the present invention had researched for seeking simple fractional quantitative determination method of isoenzyme of LDH, and as a result found that various diseases can be very easily detected by utilizing such a phenomenon that each inhibitory degree against LDH activity differs gradually from other ones according to each isoenzyme in case of reaction by adding of very small amount of LDH activity inhibitor.

Furthermore, we had examined this phenomenon in more detail, and as a result found that the LDH activity inhibitor is not a single substance but composed of two or more substances, and that the inhibitory degree varies according to the content of these inhibitors.

Among LDH activity inhibitors we had isolated the most effective substance for the fractional quantitative determination of isoenzyme of LDH as a single substance and confirmed that the single substance is 1,6-dihydro nicotinamide adenine dinucleotide having the following Formula, and thus completed the present invention:

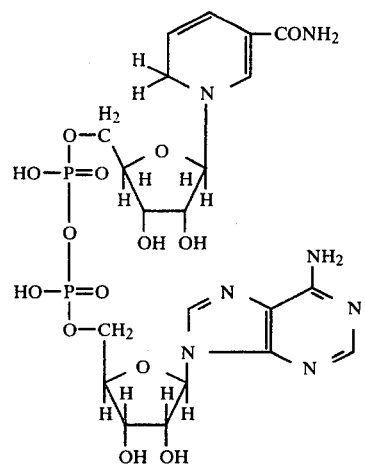

Namely, where 1,6-dihydro nicotinamide adenine dinucleotide (referred to hereinafter as 1,6-DHNAD) is employed, as a single substance, for the fractional quantitative determination of isoenzyme of LDH, it presents quite stable and constant inhibition against LDH isoenzyme, namely against H-type LDH and M-type LDH respectively, and thus can be used for an excellent fractional quantitative analytical method for LDH isoenzyme.

The determination agent of this invention is employed in case of measurement of LDH activity by using pyruvic acid as a substrate, and with respect to a sample, on the one hand, LDH activity is determined in such a situation that it is inhibited by 1,6-DHNAD; on the other hand, total LDH activity is determined in such a situation that only NAD of reduced type is added without 1,6-DHNAD, and then the ratio between the former LDH activity and the latter total LDH activity was calculated, and therefore the ratio obtained above can be compared with the standard value whose inhibitory degree of isoenzyme has been previously found, and thereby the amount of isoenzyme in the sample can be fractionally determined very easily.

Hereinafter, the method of fractional quantitative analysis will be detailed.

With respect to the samples wherein various LDH isoenzymes are contained, the various active factors are respectively expressed as in the following Table:

| Presence or absence of 1,6-DHNAD | Factor of activity | | |
|---|---|---|---|
| | Activity due to H-type LDH | Activity due to M-type LDH | Total LDH activity |
| Absent | A H | A M | A |
| Present | A'H | A'M | A' |

Namely, $A_H$, $A_M$ and A indicate respectively the activities which are obtained from the determination in case of using normal reaction solution without 1,6-DHNAD, and $A'_H$, $A'_M$ and $A'$ indicate respectively the LDH activities which are obtained from determination in case of using reaction solution containing 1,6-DHNAD above described in certain amount.

And, where the following equations are given:

$$R_H = A_H/A$$

$$R_M = A_M/A$$

$$P = A'/A$$

$$P_H = A'_H/A_H \text{ and}$$

$$P_M = A'_M/A_M,$$

the following relationship is obtained between P and $R_H$:

$$\begin{aligned} P &= A'/A & \text{equation (1)}\\ &= (A'H + A'M)/A \\ &= (PH\,AH + PM\,AM)/A \\ &= PHRH + PMRM \\ &= PHRH + PM - PMRH \\ P &= (PH - PM)\,RH + PM \end{aligned}$$

Figure 2:
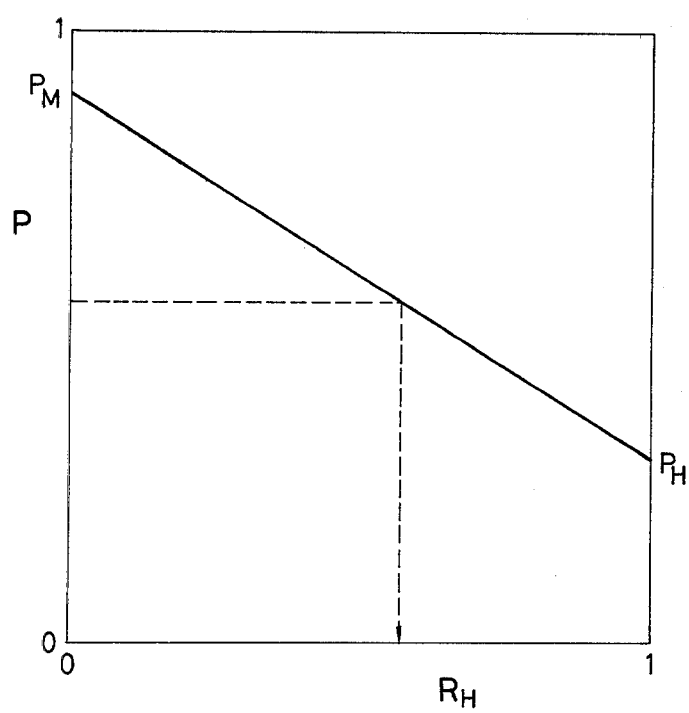
FIG. 2 is a nomograph for finding partial ratio of H-type LDH from the inhibitory degree against LDH activity.

The relationship above may be represented by a straight line, having a slope of $(P_H - P_M)$, with intercept $P_M$ on P axis as shown in the nomograph of FIG. 2 in which P is shown on the ordinate and $R_H$ is shown on the abscissa. P indicates the ratio of the activity with a certain amount of 1,6-DHNAD to that without 1,6-DHNAD, and $R_H$ indicates the ratio of activity of H-type LDH to total LDH activity.

Hence, on the one hand, by utilizing reaction solution without the activity inhibitor (reaction solution 1), reaction solution containing 1,6-DHNAD in certain amount (reaction solution 2) and 2 kinds of LDH samples in which the isoenzyme composition has been known, the standard curve is obtained; on the other hand, the unknown LDH sample is measured in the same manner, and then observed ratio P (A'/A) is referred to the standard curve, and thereby the isoenzyme composition can be determined fractionally.

According to the method of fractional quantitative determination of LDH isoenzyme, since, it contains only 1,6-DHNAD which is a single substance with respect to inhibitor, the inhibition interference never occurs due to other inhibitory substances mixed therewith, and thereby the thus obtained value is extremely reliable.

1,6-DHNAD of the present invention can be obtained by such a method that it comprises chemically reducing $NAD^+$ by borohydride or allowing to stand NAD of reduced type in an alkaline solution for 2 to 3 weeks to form a considerable amount of 1,6-DHNAD, enzymatically oxidizing only NADH in the solution, passing through DEAE-cellulose column chromatography to adsorb it, washing with buffer solution, and then eluting with sodium acetate solution to obtain 1,6-DHNAD.

Hereinafter Experimental Examples and Examples of the invention will be shown.

EXPERIMENTAL EXAMPLE 1

0.8 mM sodium pyruvate and 0.2 mM NAD of reduced type were added to 0.05 M phosphate buffer (pH 7.5) to form solution. 1,6-DHNAD was respectively added to said solution at a concentration of 0.14, 0.81, 0.90, 1.20, 4.80 and 7.6 μg/ml to prepare each reaction solution.

On the one hand, preparing H-type and M-type LDH solutions, reacting thus prepared solutions and the reaction solutions above obtained respectively, and then a test was carried out to find 1,6-DHNAD concentration wherein wide difference of inhibition degree was present against each LDH isoenzyme. With respect to LDH activity, since the absorbance of NAD of reduced type was present at 340 nm but that of oxidized type was absent, with the aid of the difference of changes in absorbance at 340 nm, the remaining activity was obtained.

The results are shown in the Table below, the difference of inhibition degree was preferable in case of inhibitor/NAD of reduced type = 1/500 − 1/20 and more particularly 1/250 − 1/32, so that it may be easily understood that such a fractional quantitative determination agent of LDH isoenzyme that contains the inhibitor and NAD of reduced type at the concentration in above range is most suitable.

| | Relative activity % | | | | | |
|---|---|---|---|---|---|---|
| 1,6-DHNAD added (μg/ml) | 0.14 | 0.31 | 0.90 | 1.20 | 4.8 | 7.6 |
| 1,6-DHNAD/ NAD of reduced type(W/W) | 1/1,100 | 1/500 | 1/170 | 1/125 | 1/32 | 1/20.1 |
| H-type LDH | 90 | 80 | 58 | 50 | 21 | 11 |
| M-type LDH | 97 | 93 | 83 | 77 | 57 | 45 |

EXPERIMENTAL EXAMPLE 2

0.8 mM sodium pyruvate, 0.2 mM NAD of reduced type and 1,6-DHNAD in an amount of 1/250 of said NAD of reduced type were added to 0.05 M phosphate buffer (pH 7.5) to prepare reaction solution.

On the other hand, various samples were prepared by combining H-type LDH and M-type LDH in varying amounts, and then these samples were treated with the reaction solution above to examine how inhibition appears according to each combination.

The results are shown in the Table below, and it is clear that the composition of H-type: M-type can be definitely determined by the fractional quantitative determination agent of the present invention.

| Isoenzyme ratio | | Total activity | Activity |
|---|---|---|---|
| | | | In case of 1,6-DHNAD/NAD of |
| H-type LDH | M-type LDH | (only NAD of reduced type) | reduced type = $\frac{1}{250}$ |
| 100 : 0 | | 130 | 87 |
| 75 : 25 | | 130 | 93 |
| 50 : 50 | | 130 | 100 |
| 25 : 75 | | 130 | 107 |
| 0 : 100 | | 130 | 113 |

EXAMPLE 1

(1) 1/10 N NaOH was added to 20% aqueous solution of NAD of reduced type, the solution was adjusted to pH 12, followed by the allowing to stand for 3 weeks at room temperature.

Only NADH in the reaction solution above was oxidized to NAD+ by use of ADH and acetaldehyde, followed by the adsorption on DEAE-cellulose column equilibrated with 10 mM Tris-acetate buffer, followed by the washing with the same buffer, followed by the concentration gradient elution with 0 to 0.2 M sodium acetate, and then the inhibitor rich parts were obtained in the fractions Nos. 50 to 56.

Figure 1:
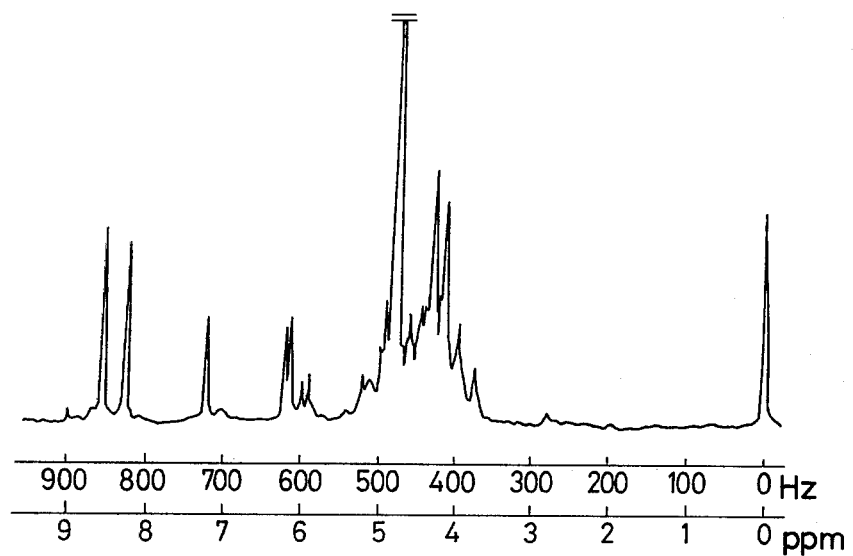
FIG. 1 shows the NMR spectrum of 1,6-DHNAD

The NMR spectrum of 1,6-DHNAD thus obtained is shown in FIG. 1.

(II) Next, 1,6-DHNAD was added to NAD of reduced type in an amount of 1/125 of said NADH to prepare fractional quantitative determination agent of LDH isoenzyme.

EXAMPLE 2

Samples were prepared by mixing hog $LDH_1$ (subunit:HHHH) (made by Boehringer Co.) and hog $LDH_5$ (subunit:MMMM) (made by Boehringer Co.) in the following ratio.

| LDH Isoenzyme Composition | | |
|---|---|---|
| Sample No. | $H_4$ Type | $M_4$ Type |
| 1 | 10 | 0 |
| 2 | 9 | 1 |
| 3 | 8 | 2 |
| 4 | 7 | 3 |
| 5 | 6 | 4 |
| 6 | 5 | 5 |
| 7 | 4 | 6 |
| 8 | 3 | 7 |
| 9 | 2 | 8 |
| 10 | 1 | 9 |
| 11 | 0 | 10 |

As reaction solutions, the solution containing 0.05 M phosphate buffer (pH 7.5), 1 mM EDTA, 0.16 mM NADH and 0.3 mM sodium pyruvate (reaction solution 1) and such one prepared by adding 2.6 μg/ml of 1,6-DHNAD to the reaction solution 1 (reaction solution 2) were respectively used.

The reactions were initiated by adding 5 μl of enzyme specimen (protein 100 μg/ml) represented in above Table to 3 ml of each reaction solution above obtained, then the diminution of absorbance at 340 nm was respectively measured by spectrophotometer.

Figure 3:
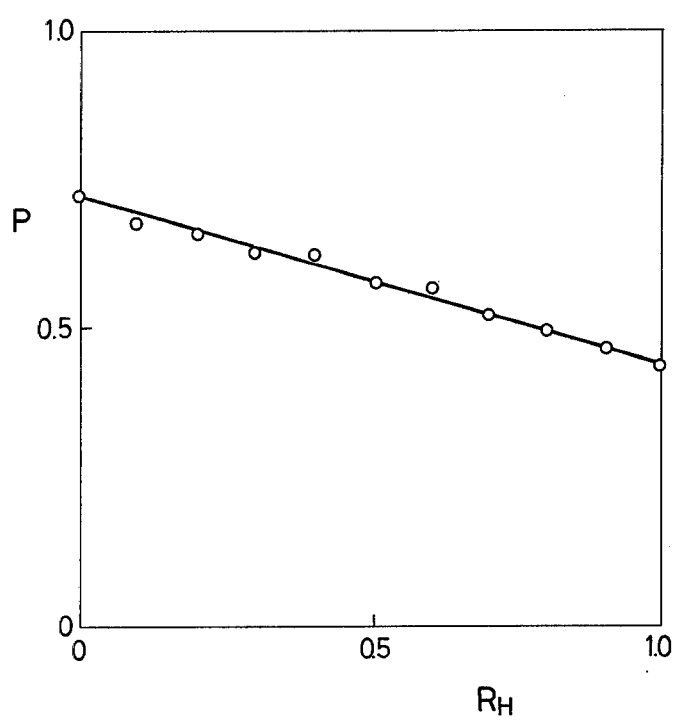
FIG. 3 is a graph showing a plot of activity ratio P against partial ratio of H-type LDH, the activity ratio P being the ratio of activity between various samples, whose isoenzyme composition has been known, in the presence or absence of 1,6-DHNAD.

The results were shown in FIG. 3 by circles. They accurately coincide with the nomograph (straight line in FIG. 3) which was obtained from the equation (1) by using hog $LDH_1$ (H-type 100%) and hog $LDH_5$ (M-type 100%).

What is claimed is:

1. A method for the fractional quantitative determination of H-type and M-type lactic dehydrogenase in a biological sample comprising:

reacting a portion of said biological sample with an aqueous solution containing pyruvate and a mixture containing 1,6-DHNAD and NADH at a rate of 1,6-DHNAD/NADH varying from 1/500 to 1/20, meanwhile reacting a second portion of said biological sample with an aqueous solution containing pyruvate and NADH, determining the ratio between lactic dehydrogenase activity obtained under the coexistent conditions of 1,6-DHNAD and NADH and lactic dehydrogenase activity obtained under non-coexistent conditions thereof, using the relationship $P = (P_H - P_M)R_H + P_M$ wherein $R_H$ equals the ratio of H-type LDH activity to total LDH activity when 1,6-DHNAD is absent;

$P_H$ equals the ratio of H-type LDH activity when 1,6-DHNAD is present, to the H-type LDH activity when 1,6-DHNAD is absent;

$P_M$ equals the ratio of M-type LDH activity when 1,6-DHNAD is present, to the M-type LDH activity when 1,6-DHNAD is absent; and P is the ratio of total LDH activity when 1,6-DHNAD is present, to the total activity when 1,6-DHNAD is absent; and comparing said ratio with a standard value of which the inhibitory degree of isoenzyme has been previously found whereby the amount of isoenzyme in the sample is fractionally obtained.

* * * * *